(12) United States Patent
Stewart et al.

(10) Patent No.: US 11,033,702 B2
(45) Date of Patent: Jun. 15, 2021

(54) ACUTE PULMONARY PRESSURIZATION DEVICE AND METHOD OF USE

(71) Applicant: The Research Foundation for the State University of New York, Brooklyn, NY (US)

(72) Inventors: Mark Stewart, East Hanover, NJ (US); Richard Kollmar, Bronx, NY (US); Krishnamurthi Sundaram, Staten Island, NY (US); Joshua Silverman, Roslyn Estates, NY (US); Ko Nakase, Tokyo (JP); Hamid Arjomandi, Brooklyn, NY (US)

(73) Assignee: The Research Foundation for the State University of New York, Brooklyn, NY (US)

( * ) Notice: Subject to any disclaimer, the term of this patent is extended or adjusted under 35 U.S.C. 154(b) by 468 days.

(21) Appl. No.: 15/772,468

(22) PCT Filed: Oct. 28, 2016

(86) PCT No.: PCT/US2016/059412
§ 371 (c)(1),
(2) Date: Apr. 30, 2018

(87) PCT Pub. No.: WO2017/075416
PCT Pub. Date: May 4, 2017

(65) Prior Publication Data
US 2018/0326171 A1    Nov. 15, 2018

Related U.S. Application Data

(60) Provisional application No. 62/248,639, filed on Oct. 30, 2015.

(51) Int. Cl.
*A61M 16/04* (2006.01)
*A61M 16/00* (2006.01)

(52) U.S. Cl.
CPC .... *A61M 16/0472* (2013.01); *A61M 16/0096* (2013.01); *A61M 2202/0208* (2013.01); *A61M 2205/8225* (2013.01)

(58) Field of Classification Search
CPC ............ A61M 16/0472; A61M 16/201; A61M 16/0477
See application file for complete search history.

(56) References Cited

U.S. PATENT DOCUMENTS 3,886,946 A * 6/1975 Hyde ................ A61M 16/0472
128/207.29
4,091,816 A 5/1978 Elam
(Continued)

FOREIGN PATENT DOCUMENTS

SU    1724259 A1    4/1992

OTHER PUBLICATIONS

Ruskin, Keith J., Rosenbaum, Stanley H., Anesthesia emergencies, 2011, Oxford University Press.
(Continued)

*Primary Examiner* — Samchuan C Yao
*Assistant Examiner* — Cana A Gallegos
(74) *Attorney, Agent, or Firm* — Hoffberg & Associates; Steven M. Hoffberg (57) ABSTRACT

A system and method for relief of negative lung pressure during acute laryngospasm or upper airway obstruction, providing a non-toxic gas cartridge capable of supplying between 0.5-5 liters of gas during a procedure, a valve adapted to commence and stop gas release, and a trans-cricothyroid cartilage inflation needle for acutely relieving the negative pressure in the chest. The needle may also be used to insert a guidewire to assist in endotracheal tube insertion.

20 Claims, 4 Drawing Sheets

(56) References Cited

U.S. PATENT DOCUMENTS

| | | | |
|---|---|---|---|
| 4,538,606 A | | 9/1985 | Whited |
| 4,677,978 A | | 7/1987 | Melker |
| 4,700,700 A | | 10/1987 | Eliachar |
| 4,898,163 A | | 2/1990 | George |
| 5,507,279 A | * | 4/1996 | Fortune ............. A61M 16/0472 |
| | | | 128/200.26 |
| 5,558,081 A | | 9/1996 | Lipkin |
| 5,591,186 A | * | 1/1997 | Wurster ............. A61B 17/3417 |
| | | | 604/164.12 |
| 5,938,591 A | | 8/1999 | Minson |
| 6,402,770 B1 | | 6/2002 | Jessen |
| 7,036,460 B2 | | 5/2006 | Ducharme et al. |
| 7,644,714 B2 | | 1/2010 | Atkinson et al. |
| 7,849,857 B2 | | 12/2010 | Gobel |
| 7,909,758 B2 | | 3/2011 | Shapiro |
| 7,934,506 B2 | | 5/2011 | Woodson et al. |
| 7,975,700 B2 | | 7/2011 | Frazier et al. |
| 7,992,567 B2 | | 8/2011 | Hirotsuka et al. |
| 7,997,266 B2 | | 8/2011 | Frazier et al. |
| 8,074,655 B2 | | 12/2011 | Sanders |
| 8,080,014 B2 | | 12/2011 | Roue et al. |
| 8,186,355 B2 | | 5/2012 | van der Burg et al. |
| 8,220,466 B2 | | 7/2012 | Frazier et al. |
| 8,246,550 B2 | | 8/2012 | Morris |
| 8,777,958 B2 | | 7/2014 | Roue et al. |
| 8,788,036 B2 | | 7/2014 | Lindenthaler |
| 8,821,495 B2 | | 9/2014 | van der Burg et al. |
| 9,022,024 B2 | | 5/2015 | Frazier et al. |
| 9,375,576 B2 | | 6/2016 | Pitman |
| 2008/0071245 A1 | | 3/2008 | Muller et al. |
| 2008/0091247 A1 | | 4/2008 | Muller et al. |
| 2011/0093032 A1 | | 4/2011 | Boggs et al. |
| 2011/0178529 A1 | | 7/2011 | Muller et al. |
| 2011/0301587 A1 | | 12/2011 | Deem et al. |
| 2012/0172909 A1 | | 7/2012 | Mathis et al. |
| 2013/0131551 A1 | | 5/2013 | Raghunathan et al. |
| 2013/0226026 A1 | | 8/2013 | Dillard et al. |
| 2014/0090644 A1 | * | 4/2014 | Aldana .................. A61M 16/12 |
| | | | 128/203.23 |
| 2014/0228759 A1 | | 8/2014 | Soma et al. |
| 2015/0283345 A1 | * | 10/2015 | Enk .................... A61M 16/0438 |
| | | | 128/204.23 |

OTHER PUBLICATIONS

Rex, M.A.E., A Review of the Structural and Functional Basis of Laryngospasm and a Discussion of the Nerve Pathways Involved in the Reflex and its Clinical Significance in Man and Animals, British Journal of Anaesthesia, 1970, 891-899.

Thomas, John A MD., Hagberg, Carin A MD., Chapter 30 the Difficult Airway: Risks, Prophylaxis, and Management, Chestnut's Obstetric Anesthesia: Principles and Practice E-Book, 2014, 651-676.

Vaida, Sonia, Clinical Practice Guidelines for the Management of the Difficult Airway in Obstetric Anesthesia, 2008 ATI Timisoara.

Stoohs RA, Blum HC, Knaack L, Butsch-von-der-Heydt B, Guilleminault C., Comparison of pleural pressure and transcutaneous diaphragmatic electromyogram in obstructive sleep apnea syndrome., Sleep. Mar. 2005;28(3):321-9.

Calder, Ian, Pearce, Adrian, Core Topics in Airway Management, Cambridge University Press, 2005.

Mace, Sharon E., Hedges, Jerris R., Chapter 6 Chricothyrotomy and Translaryngeal Jet Ventilation, Clinical Procedures in Emergency Medicine, 4th Edition, 2003.

Hamaekers, A. E., Henderson, J.J., Equipment and strategies for emergency tracheal access in the adult patient, Anaesthesia, 2011, 66 (Suppl. 2), pp. 65-80.

Helfenbein, Eric, Firoozabadi, Reza, Chien, Simon, Carlson, Eric, Babaeizadeh, Saeed, Development of three methods for extracting respiration from the surface ECG: A review, Journal of Electrocardiology vol. 47, Issue 6, Nov.-Dec. 2014, pp. 819-825.

Muller, N., Gulston, G., Cade, D., Whitton, J., Froese, A.B., Bryan, M.H., Bryan A.C., Diaphragmatic muscle fatigue in the newborn, Journal of Applied Physiology Published Apr. 1, 1979, vol. 46, No. 4, 688-695.

Sharp, John T., Druz, Walter S., Kondragunta, Venkata R., Diapgragmatic Responses to Body Position Changes in Obese Pateints with Obstructive Sleep Apnea, American Review of Respiratory Disease, Nov. 13, 1984.

Henderson, J.J., Popat, M.T., Latto, I.P., Pearce, A.C., Difficult Airway Society guidelines for management of the unanticipated difficult intubation, Anaesthesia, 2004, 59, pp. 675-694.

Dickison, Anne, Improvisational Airway Management, Second World Congress Wilderness Medical Society, Friday, Aug. 11, 1995.

Rajkumar, S.A., Infraglottic Invasive Airways, Presentation (>2003).

Chien, M.Y., Wu, Y.T., Lee, P.L., Chang, Y.J., Yang, P.C., Inspiratory muscle dysfunction in patients with severe obstructive sleep apnoea, European Respiratory Journal 2010 35: 373-380.

Aloy, Alexander, Grasl, Matthaeus, Chapter 9, Endoscopy of Larynx and Trachea with Rigid Laryngo-Tracheoscopes Under Superimposed High-Frequency Jet Ventilation (SHFJV), 2013.

George, E, Haspel, KL, The Difficult Airway, International anesthesiology clinics, 2000.

Bonnano, F.G., Issues of critical airway management (Which anesthesia; which surgical airway?), Journal of emergencies, trauma, and shock, 2012.

De la Eva, Roland C., Baur, Louise A., Donaghue, Kim C., Waters, Karen A., Metabolic correlates with obstructive sleep apnea in obese subjects, The Journal of Pediatrics vol. 140, Issue 6, Jun. 2002, pp. 654-659.

Freilich, Robert A., Lopata, Melvin, Lourenco, Ruy V., Mouth Occlusion Pressure and EMG of the Diaphragm in the Waking and Sleeping States, Advances in Experimental Medicine and Biology, vol. 99, pp. 143-149.

Mace, Sharon E., Khan, Nazeema, Needle Cricothyrotomy, Emergency Medicine Clinics of North America vol. 26, Issue 4, Nov. 2008, pp. 1085-1101.

Mittal, Manoj K, Needle cricothyroidotomy with percutaneous transtracheal ventilation, uptodate.com, 2014.

McNamara, Frances, Sullivan, Colin E., Obstructive sleep apnea in infants: Relation to family history of sudden infant death syndrome, apparent life-threateningevents, and obstructive sleep apnea, The Journal of Pediatrics vol. 136, Issue 3, Mar. 2000, pp. 318-323.

Guilleminault, Christian, Hilla, Michael W., Simmonsa, F. Blair, Dementa, William C., Obstructive sleep apnea: Electromyographic and fiberoptic studies, Experimental Neurology vol. 62, Issue 1, Oct. 1978, pp. 48-67.

Dhonneur, G. MD; Combes, X. MD; Leroux, B. MD; Duvaldestin, P. MD, Postoperative Obstructive Apnea, Anesthesia & Analgesia: Sep. 1999—vol. 89—Issue 3—p. 762.

Renolleau, Sylvain, Letourneau, Patrick, Niyonsenga, Théophile, Praud, Jean-Paul, Thyroarytenoid Muscle Electrical Activity During Spontaneous Apneas in Preterm Lambs, Am J Respir Crit Care Med vol. 159. pp. 1396-1404, 1999.

Maarsingh, E. J. W., Van Eykern, L. A., Sprikkelman, A.B., Hoekstra, M. O., van Aalderen, W. M. C., Respiratory muscle activity measured with a noninvasive EMG technique: technical aspects and reproducibility, Journal of Applied Physiology Jun. 1, 2000 vol. 88 No. 6, 1955-1961.

Kuna, S.T., Smickley, J., Response of genioglossus muscle activity to nasal airway occlusion in normal sleeping adults, Journal of Applied Physiology Jan. 1, 1988 vol. 64 No. 1, 347-353.

Hart, Kristopher L., Thompson, Stevan H., Emergency Cricothyrotomy, Atlas Oral Maxillofacial Surg Clin N Am 18 (2010) 29-38.

Wulbrand, H., Von Zezschwitz, G., Bentele, K. H. P., Submental and Diaphragmatic Muscle Activity during and at Resolution of Mixed and Obstructive Apneas and Cardiorespiratory Arousal in Preterm Infants, Pediatric Research, vol. 38, No. 3, 1995.

Rudra, A., Chatterjee, S., Tracheal Extubation in the Difficult Airway, Indian J. Anaesth. 2006; 50 (6) : 430-434.

Steward, D., Transtracheal Jet Ventilation. II, Canadian Journal of Anaesthesia 42(6):554-555 • Jun. 1995.

(56) References Cited

OTHER PUBLICATIONS

Issa, F.G., Sullivan, C.E., Upper airway closing pressures in obstructive sleep apnea, Journal of Applied Physiology Aug. 1, 1984 vol. 57 No. 2, 520-527.
Boyce, J.R., Peters, G., Vessel dilator cricothyrotomy for transtracheal jet ventilation, Can J. Anaesth 1989 / 36:3 / pp. 350-335.
ISR for PCT/US16/059412 (Feb. 2, 2017).

* cited by examiner

ACUTE PULMONARY PRESSURIZATION DEVICE AND METHOD OF USE

CROSS REFERENCE TO RELATED APPLICATIONS

The present application is a National Stage application claiming priority under 35 U.S.C. § 371 to PCT Patent Application No. PCT/US16/59412, filed Oct. 28, 2016, which claims benefit of priority under 35 U.S.C. § 119(e) to U.S. Provisional Patent Application No. 62/248,639, filed Oct. 30, 2015, the entirety of which are expressly incorporated herein by reference.

FIELD OF THE INVENTION

The present invention relates to the field of transtracheal jet ventilation devices, and more particularly to an acute intervention device for reoxygenation during complete airway obstruction and for alleviating pulmonary edema resulting from laryngospasm.

BACKGROUND OF THE INVENTION

Acute upper airway obstruction can occur by different mechanisms, but the results of complete obstruction are all the same: rapid hypoxemia and respiratory and/or cardiac arrest leading to death. Even when the obstruction is cleared, hypoxia persists because of significant pulmonary edema.

Laryngospasm is an acute medical emergency that typically resolves after a few minutes, but may lead to pulmonary edema due to negative pressures due to inhalation attempts and diaphragmatic expansion of the lungs against a blocked airway. Laryngospasm may be triggered when the vocal cords or the area of the trachea below the vocal folds detects the entry of water, mucus, blood, foreign body, or other substance, or during an epileptic seizure.

Laryngospasm is an uncontrolled/involuntary muscular contraction (spasm) of the vocal folds. In non-emergency circumstances, the condition typically lasts less than 60 seconds, and causes a partial blocking of inspiration, while exhalation remains easier. In a more serious form, inhalation is blocked and exhalation severely restricted, and the condition may last several minutes. This more serious form, is a medical emergency, in that ventilation and oxygenation is compromised, and the asymmetry of ventilation leads to negative pulmonary pressures and pulmonary edema which may be life threatening or fatal. Laryngospasm may also lead to cardiac arrest within 30-45 seconds in children.

A urethane/kainate animal model of epilepsy has been an innovative tool to study autonomic nervous system consequences during seizures and for exploring the absolute limits of ANS activation on cardiac function [4,5,10-13,15,16]. The rat model was expanded to permit detailed study of laryngeal and respiratory physiology during seizure activity, including video laryngoscopy of vocal fold movement with movement quantitation, and simultaneous recordings of recurrent laryngeal or superior laryngeal nerve activity, laryngeal muscle EMG, pulse oximetry, plethysmography, EEG and ECG [7]. Periods of obstructive and central apnea during seizure activity were recorded. Seizure-induced laryngospasm resulted in obstructive apnea with rapid, hypoxic changes in the ECG, but central apneic periods did not. Severe laryngospasm likely represents a contributor to the seizure and hypoxemia-induced conditions that result in death.

Laryngospasm is typically a transient protective response to laryngeal irritation meant to prevent aspiration. Laryngospasm has been observed during seizures or postictally, evidenced by stridor and a narrowed airway when attempting to place an endotracheal tube [17] or intensive inspiratory effort with severe air hunger [1]. Cats and piglets experienced hypoventilation and glottal obstruction (due to tonically adducted vocal folds) during chemically-induced seizures [6, 18, 19]. Pulmonary edema is the most common single finding at autopsy in Sudden Unexpected Death in Epilepsy (SUDEP) cases is also indirect evidence of laryngospasm [2, 8, 14, 55]. Ictal hypoventilation has been reported in several animal models of seizures. A report indicated that a patient dies as a consequence of obstructive apnea due to laryngospasm. Severe postictal laryngospasm as a potential mechanism for sudden unexpected death in epilepsy: a near-miss in an EMU [56].

Pulmonary edema occurs when "pulling" against a closed airway—the inspiratory effort increases pulmonary capillary pressure [3,9,21]. Pulmonary edema can also occur when the upper airway obstruction is removed (Post-obstructive pulmonary edema, type 2; [20]). Rather than a reflex response to laryngeal irritation, seizure spread into medullary motor regions that include the recurrent laryngeal nerve may drive laryngospasm, making it a significant contributor to hypoxemia. A critical aspect of pulmonary edema is that it can significantly outlast the seizure and laryngospasm.

Laryngospasm can be severe during epileptic seizures, leading to complete obstructive apnea. During periods of obstructive apnea, cardiac rhythm changes indicative of hypoxia (e.g. ST segment changes) occur within tens of seconds and rats experience respiratory arrest in about 60 seconds. Additionally, when the laryngospasm ends, a persistent decreased oxygen saturation may occur, likely due to pulmonary edema. In epileptic patients that have died suddenly, pulmonary edema is the most common autopsy finding.

The effort to breathe exists during the time of obstruction and this effort increases as the duration of obstruction increases. The large negative pressures developing within the alveoli from pulling against a closed glottis is likely to be a significant contributor to the development of pulmonary edema. Hypoxia triggers various cellular responses, including the production and release of VEGF that can chemically increase leakage of plasma into the interstitial space around alveoli.

Pulmonary edema impairs gas exchange for times that last much longer than the period of obstruction.

More generally, pulmonary edema is a known consequence of extended laryngospasm. See, [21-54], each of which is expressly incorporated herein by reference in its entirety, U.S. Pat. No. 4,898,163, expressly incorporated herein by reference, relates to a transtracheal airway and placement device. The device is used to establish an airway in transtracheal intubation via puncture of the cricothyroid membrane with a curved needle. The integrated design is argued to provide quick and accurate placement of the airway in both emergency and non-emergency applications.

The typical methods of maintaining a patient's airway are by anatomical positioning, clearing the passageway of foreign materials, positive pressure mask ventilation, oral/nasal airways, or oral/nasal approach to tracheal intubation. Following failure of all of the typical methods of ventilation, the last method of resort is transtracheal intubation via formal tracheostomy or cricothyrotomy. These procedures, though infrequently required, are recommended for use as a last means method. See, Clinics of Anesthesiology, Tunstall and Sheikh, 1986, expressly incorporated herein by reference.

In many patients, establishment of the airway may be formidable due to morphological anomalies, such as a large tongue, excessive soft tissue or tracheal displacement. Inabilities of the patient to extend the head and neck or to open the mouth wide enough contribute to the difficulty of maintaining the airway, as do other morphological anomalies or physiological events such as floppy epiglottis or laryngospasm.

Even the use of formal tracheostomy presents inherent problems. Tracheostomy requires instrumentation which may not be available in emergency situations. Additionally, given the time constraints involved in an emergency, a tracheostomy may yield to the more expedient procedure of cricothyrotomy. Circothyrotomy, considered by many to be the preferred method of establishing an airway after other methods have failed, is achieved by transtracheal intubation via a percutaneous puncture through the cricothyroid membrane into the trachea.

U.S. Pat. No. 4,677,978, expressly incorporated herein by reference, describes a method for establishing a transtracheal airway. Once the percutaneous placement of the needle is made, the needle and syringe are removed so that a guide wire can be placed through the catheter.

SUMMARY OF THE INVENTION

The present technology provides a method for supporting oxygen saturation levels and alleviating negative pulmonary pressure during acute obstructive airway emergencies.

The technology employs a transtracheal puncture device is inserted in the neck, along the centerline, through the cricothyroid cartilage below the vocal cords, and a jet of gas is produced, alleviating the negative pressure in the lungs, and reducing the possibility of pulmonary edema.

Because the device is intended to provide immediate relief of negative pressure, and not itself to ensure a patent airway or oxygenation, the gas does not need to be air or oxygen, and thus the device may avoid fire hazards which may result from compressed air or compressed oxygen. The source of pressurized gas may be, for example, a 15-16 gram $CO_2$ cartridge or a 12 gram $N_2$ cartridge. Use of oxygen, normal or oxygen-enriched air for inflation has the added benefit of temporary oxygenation support and is recommended.

The source of pressurized gas may also be an electrically operated fan, pump or compressor. A battery of other power source may be provided to operate the electrically operated fan, pump or compressor. A simple control such as a switch may be provided, or a more complex control system such as a microprocessor which is controlled to inflate the lungs and maintain inflation, without overpressurizing.

The injection cannula may be sufficiently short to avoid risk of over-insertion, and may have a stop surface which rests against the neck when fully inserted.

The inflator preferably has a trigger to permit manual control over inflation volume. The user therefore can look at the patient's neck and chest, and press the inflator until the negative pressure is relieved. Alternately, an automated control may be provided to regulate the pressure to a neutral pressure, while avoiding over-pressure and risk of pneumothorax. The whole system is configured to provide the necessary time to establish an airway and save a life. Likewise, while the device is invasive, it is sufficiently minimally invasive to be usable in circumstances short of "last resort". That is, when a caregiver or responder observes negative airway pressures, such as retracted neck tissue, abdominal intrusion, or breathing muscle strain, the device may be used immediately, in order to provide a few minutes for measures to establish a patent airway or intubation.

Protection from the edema could be achieved by inflating the lungs below the level of the obstruction, to pressurize the airway and prevent the negative pressure that leads to acute pulmonary edema. In rat studies this hypothesis was tested, and inflation with pure oxygen, pure nitrogen, or room air all successfully protected rats against persistent low oxygen saturation levels.

The device enables an intervention that supports the individual during the obstruction, especially when oxygen or air is used as the inflation gas, but most importantly, prevents the pulmonary edema development so that recovery from an obstruction is rapid.

Laryngospasm can occur under different circumstances and the establishment of a proper airway (usually intubation in spite of spastic closure of the airway) can be difficult or impossible. The device according to the present technology may optionally include a guidewire system, to pass a guidewire, through the trachea, into the pharynx, thus facilitating intubation.

It is therefore an object to provide a device for relief of negative lung pressure after acute upper airway obstruction, comprising: a source of compressed gas suitable for inflation of human lungs; a valve, configured to control a release of the compressed gas; a hollow inflation needle having a sharp tip configured to pierce through the skin and cricothyroid cartilage into the larynx or the through the skin and tracheal cartilage into the trachea, and a valve interface configured to receive compressed gas air from the valve of between about 1-60 liters per minute; and a stop configured to establish an insertion limit for the inflation needle into a human larynx or trachea.

It is also an object to provide a device for relief of negative lung pressure after acute upper airway obstruction, comprising: a source of compressed gas suitable for inflation of human lungs; a control, configured to control a flow of the compressed gas into the human lungs; a hollow inflation needle having a sharp tip configured to pierce through the skin and cricothyroid cartilage into the larynx or the through the skin and tracheal cartilage into the trachea, a valve interface configured to receive a controlled release of compressed air from the valve of between about 1-20 liters per minute, and to retain the inflation needle to the valve; and a stop configured to establish an insertion limit for the inflation needle into a human trachea.

It is a further object to provide a method for relieving negative lung pressure after acute upper airway obstruction of a human, comprising: providing a device comprising a source of compressed gas suitable for inflation of human lungs; a control, configured to selectively control a flow of the compressed gas; a hollow inflation needle having a sharp tip configured to pierce through the skin and cricothyroid cartilage into the larynx or through the tracheal cartilage into the trachea, an interface configured to receive a controlled flow of compressed gas from the control of between about 1-60 liters per minute; and a stop configured to establish an insertion limit for the inflation needle into a human trachea; assessing an upper airway status of the human; inserting the inflation needle through the skin and cricothyroid cartilage into the larynx or tracheal cartilage into the trachea; and controlling inflation from the source of compressed gas, through the inflation needle, into the larynx or trachea, to alleviate the negative lung pressure.

It is another object to provide a method of preventing pulmonary edema from acute upper airway obstruction, comprising: providing a source of compressed gas suitable for inflation of lungs without substantial acute toxicity; assessing a respiratory status; inserting a hollow inflation needle having a sharp tip, through the skin into the larynx or trachea; and controlling a release of the compressed gas with a valve, at a rate of between about 1-60 liters per minute, to relieve the negative pressure. The method may further comprise inserting a guidewire through the inflation needle into the larynx or trachea; extending the guidewire upward through the larynx, past an upper airway obstruction; connecting the guidewire to a tube; and guiding the tube down past the upper airway obstruction by retracting the guidewire.

It is a still further object to provide a method of preventing or relieving hypoxemia from acute upper airway obstruction, comprising: providing a source of compressed gas comprising at least 15% oxygen; inserting a hollow inflation needle having a sharp tip, through the skin into the larynx or trachea; and controlling a release of the compressed gas with a valve, at a rate of between about 1-60 liters per minute, to relieve the hypoxemia.

The hollow inflation needle preferably has a closed tip and a side exhaust port for the compressed gas. Alternately, the hollow inflation needle may have an aperture at its tip.

The hollow inflation needle may be configured to be selectively retained to a valve.

The device may be part of a kit, which includes a guidewire configured to pass through the inflation needle. The guidewire, for example, may have a looped end. The looped end, in turn, is configured to pass through the hollow inflation needle, into the larynx or trachea. A hooked structure, for example on a tube or endotracheal tube, can then be attached to the guidewire, to assist in passing the tube or endotracheal tube past the upper airway obstruction. The hollow inflation needle may thus have a closed tip and a side exhaust port for the compressed gas, wherein the guidewire is configured to pass through the inflation needle and upon advancement, deflect through the side exhaust port.

The compressed gas may comprise compressed air, oxygen, nitrogen, or carbon dioxide, helium, argon, or other non-acutely toxic gas, for example. To facilitate blood oxygenation, air or oxygen is generally preferred. However, in environments where oxidizers are contraindicated, a gas may be used which is non-flammable. The source of compressed gas may comprise between about 10-30 grams of gas, suitable for inflation of adult lungs, or 4-10 grams of gas, suitable for inflation of children's lungs. By limiting the amount of gas present n a cartridge, the risk of hyperinflation is reduced.

The control may be a valve which comprises a finger trigger, actuatable to initiate a flow of gas into the larynx or trachea.

The source of compressed gas may comprise a cartridge having a threaded neck for attachment to the valve.

The valve or control may comprise a pressure regulator and/or a tinier.

The inflation needle may have a diameter of about 1 mm and a conical or chiseled tip. The inflation needle may include an internal surface (within the hollow space) inclined with respect to an axis of the needle to deflect an inserted guidewire out through a sidewall aperture.

Since the device is typically used when upper airway obstruction is present, after alleviating negative lung pressure by inflating the lungs, efforts may be immediately begun to establish a functional airway. A Guidewire may be inserted through the inflation needle into the larynx or trachea, which can then be used to pull a tube, e.g., an endotracheal tube, from the mouth, past the obstruction. Advantageously, the guidewire has a looped end, and the tube is provided with a hook or other attachment for affixation to the loop, to permit a tension to be applied to the tube, and pulling it past the obstruction. The method may thus comprise providing the device and a tube, having a hook adapted for connection to the looped end; connecting the looped end to the tube; and guiding the tube through the upper airway obstruction by retracting the guidewire.

The control may comprise a valve having a pressure regulator. The pressure regulator may sense a pressure within the larynx or trachea below the upper airway obstruction, with the flow of gas controlled dependent on the sensed pressure. A pressure regulator may also be provided to normalize a pressure from a compressed gas cylinder to the hollow inflation needle.

The hollow inflation needle is preferably configured to exhibit minimal trauma to the tissues during insertion, and thus should be sharp, with the extend of insertion limited by a stop to avoid piercing the hack wall of the trachea or larynx.

The flow rate of compressed gas through the hollow inflation needle is preferably 3-20 liters per minute.

DETAILED DESCRIPTION OF THE PREFERRED EMBODIMENTS

Figure 1:
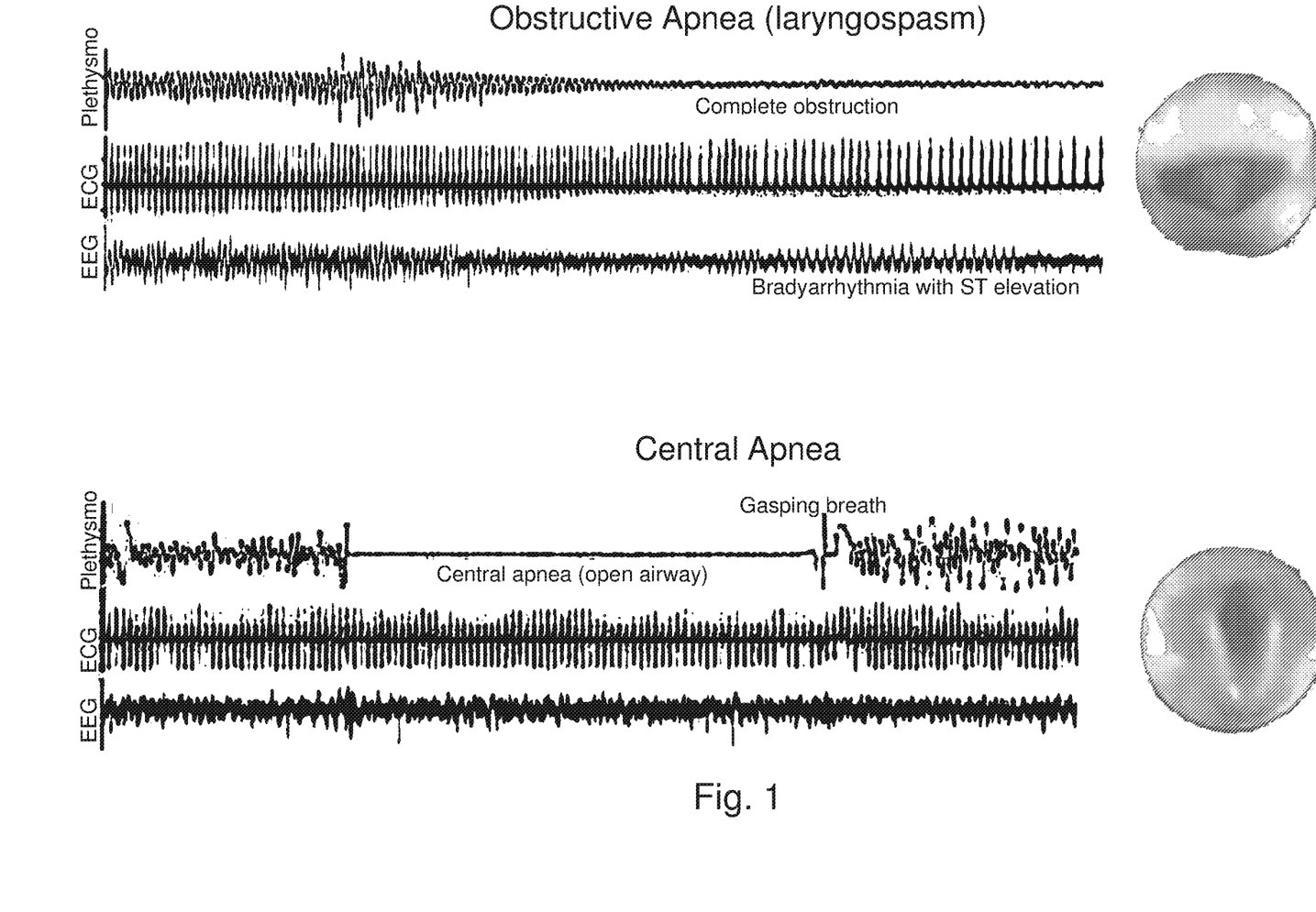
FIG. 1 shows graphs of rapid desaturation during seizure-induced laryngospasm.

FIG. 1 shows the rapid oxygen desaturation during seizure-induced laryngospasm. The short time-course for hypoxic changes in ECG (within tens of seconds), indicates the extremely short, timeframe for intervention. In the top panel, an episode of obstructive apnea is shown as evidenced by the absence of airflow on head-out plethysmography and the hypoxic ECG changes within tens of seconds. For comparison, a period of seizure-induced central apnea (where the airway is open) is shown that presents no such hypoxic changes even though the animal is not breathing. Airway closure from laryngospasm to produce obstructive apnea was fatal in 7/7 rats.

Figure 2:
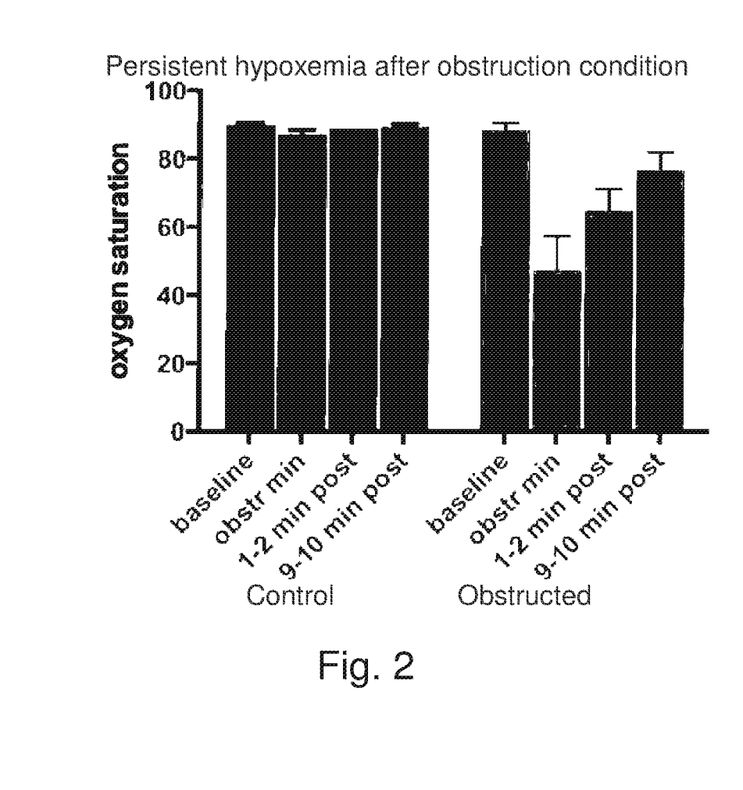
FIG. 2 shows a severe reduction in oxygen saturation during upper airway obstruction and persistence of decreased oxygen saturation after obstruction is cleared.

FIG. 2 shows severe reduction in oxygen saturation during upper airway obstruction and persistence of decreased oxygen saturation after obstruction is cleared. Shown to the left (blue bars) are the results from control animals (N=4), and to the right are the obstructed animals. Urethane-anesthetized rats received a tracheal tube that was tightly sealed in the tracheal below the larynx. Control animals received no further manipulation, but the obstructed animals were obstructed by occluding the tracheal tube for a period of 100 seconds or until the animal displayed respiratory arrest. Animals were immediately resuscitated (as necessary) by chest compressions. The set of bars for each group represent: (1) the baseline oxygen saturation as derived from the average of 5 points separated by 10 seconds; (2) the minimum oxygen saturation value during the period of obstruction; (3) the average saturation during the 60-sec period of 1 to 2 minutes after the obstruction was removed; and (4) the average saturation during the 60-sec period of 9-10 minutes after the obstruction was removed.

A 2-way repeated measures ANOVA showed significant effects for condition and for group (condition: F (3,21) =6.070, P=0.0038; group: F (1, 7)=44.69, P=0.0003) with significant differences for the obstruction minimum and at 1-2 minutes post-obstruction (P=6.838453 e-006, P=0.00257923, respectively).

To test the impact of the lung inflation method according to the present technology, rats under the same conditions as shown in FIG. 1 were studied. Lung inflation was tested with 100% oxygen gas, 100% nitrogen gas, or room air.

As shown in FIG. 2, all three gas inflation methods eliminated the persistent lower oxygen saturation after the obstruction was cleared. All animals with inflation (irrespective of the gas used for inflation) rapidly and persistently returned to baseline levels of oxygen saturation, indicating protection from persistent oxygen absorption derangements. Inflation with oxygen had the added benefit of delaying the desaturation and reducing tis minimum during the period of obstruction.

Figure 3:
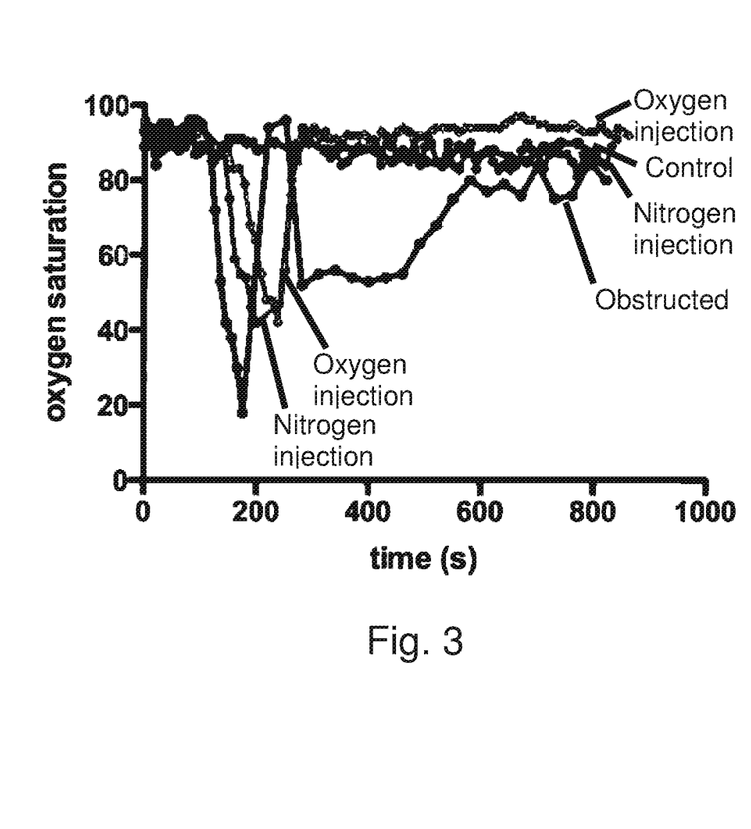
FIG. 3 shows the prevention of persistent oxygen desaturation problems by lung inflation with pure oxygen or other gas.

FIG. 3 shows the prevention of persistent oxygen desaturation problems by lung inflation with pure oxygen or other gas. The impact of lung inflation is two-fold: inflation with any gas prevents the persistent lower oxygen saturation after the upper airway obstruction is cleared, and delays and decreases the desaturation during obstruction. Only inflation with oxygen or nitrogen shown.

Evident from the data shown in FIG. 3 is the need for intervention in less than a minute. This is far too short for a call for emergency services and treatment by an emergency specialist. The volumes of air used for protection in the proof-of-concept experiments are 2-3 times the tidal volume. In rats the volume for inflation was 4.5 to 6.5 ml. In humans, where the tidal volume is reported to be about 0.5 liters, 1.0-1.5 liters would be comparable to the volumes used in the rat experiments (well below the total lung capacity of 4-6 liters).

Example 1

Jet Inflation Device

The present technology provides a simple emergency intervention based on inflation of the lungs with a modest volume of oxygen or other gas to protect a human or animal from rapid oxygen desaturation, to restore oxygen saturation levels to safe levels, and to reduce post-obstructive pulmonary edema due to a temporary upper airway obstruction or to permit longer times for clearing an obstruction. The ability to activate this intervention within seconds is critical for saving lives. Whereas the device relates to transtracheal jet ventilation, transtracheal jet ventilation is contraindicated in complete upper airway obstruction because transtracheal jet ventilation is intended for ventilation over many minutes or longer [Yealy D M, Menegazzi J J, Ward K R. Transtracheal jet ventilation and airway obstruction. Am J Emerg Med. 1991 Mar. 9(2):200]. The proposed device is intended for immediate life support over a period of up to several minutes during complete airway obstruction due to laryngospasm.

Figure 4A:
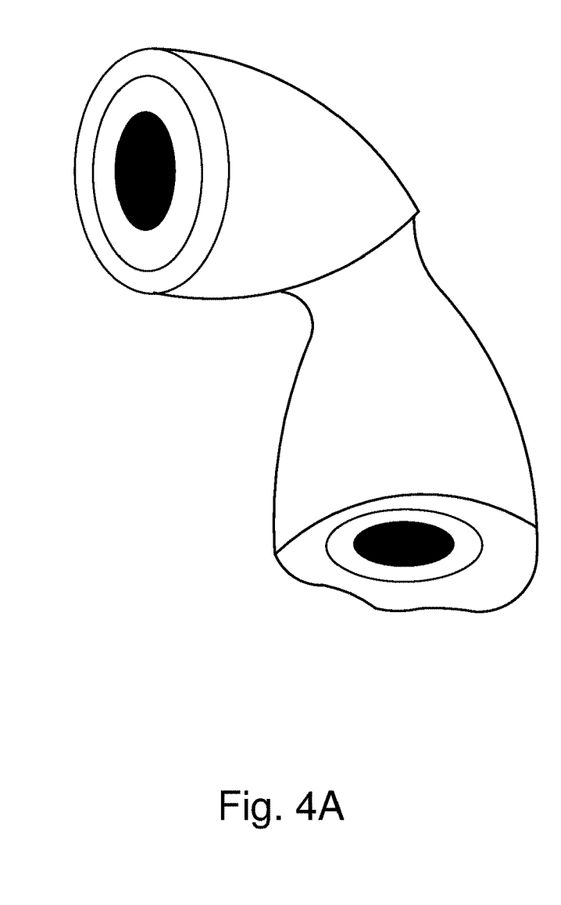
FIGS. 4A-4B shows a prior art cartridge inflation kit for repair of bicycle tires.
Figure 4B:
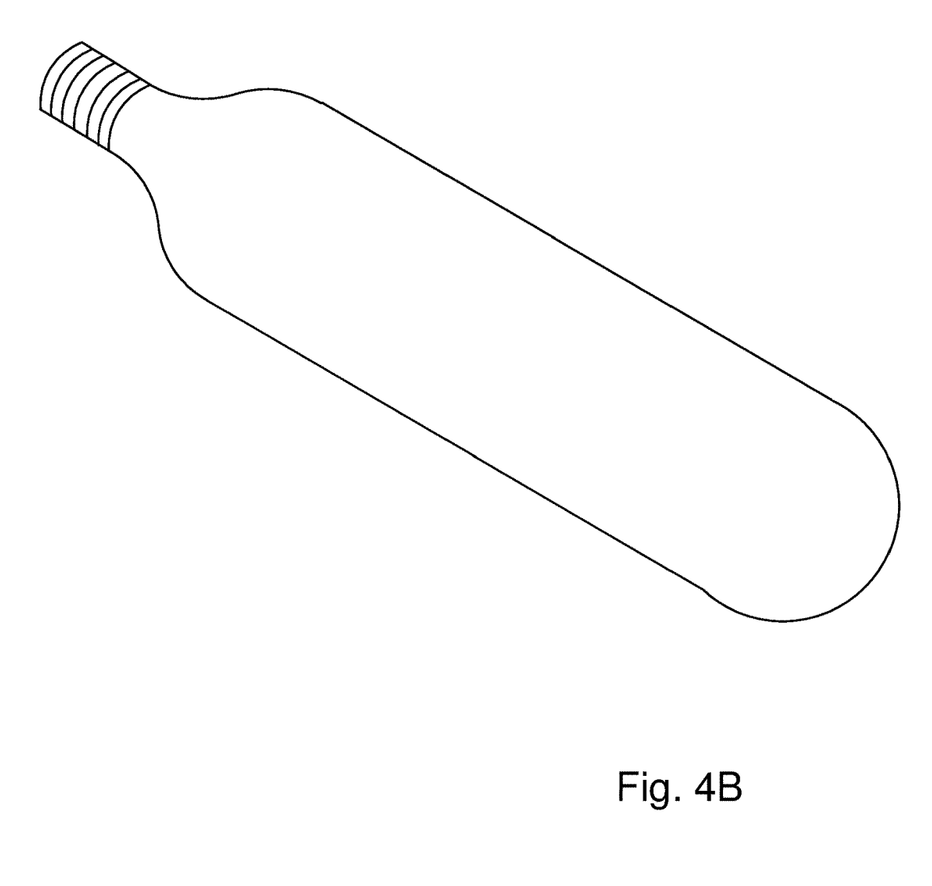

To quickly force a volume of about 2 liters into the trachea, below an upper airway obstruction, a device is provided that resembles a device used for emergency repair of bicycle tires, as shown in FIG. 4A. A 16 gram $CO_2$ cartridge (20 ml internal volume), shown in FIG. 4B, contains about 5 liters of gas at atmospheric pressure and room temperature, and can fill a bicycle tire to about 120 psi. Nitrogen, Oxygen and air (12 grams) may be provided in a similar size cartridge. These cartridges are sealed and stored stably under normal temperatures, and can typically be shipped by ground. A simple regulator screws or presses onto the cylinder, and is used to both regulate the rate at which gas is released. The regulator typically has a threaded or clamped attachment for an inflation cannula or valve stem attachment.

The present device has a similar configuration, with a typical canister capacity of 2-6 liters (standard temperature and pressure) for a single use, or larger to permit multiple inflations. Because of their physiologic effects carbon dioxide, oxygen, nitrogen or air are the preferred gasses, but carbon dioxide may be used in some cases.

FIG. 4A shows a prior art, commercially available cartridge inflation kit for repair of bicycle tires. This may employ carbon dioxide or nitrogen cartridges, shown in FIG. 4B. See, Genuine Innovations "Tire Repair and Inflation Kit", Microflate Nano EBTB 50, Accessories Marketing, Inc., Div. of ITW Inc., San Luis Obisbo Calif., SKU 708162025816, which has a cap that screws onto the threaded cartridge to break the frangible metal cartridge seal. Unscrewing the cap starts and regulates the rate of flow. Other models have trigger actuated valves.

Figure 5A:
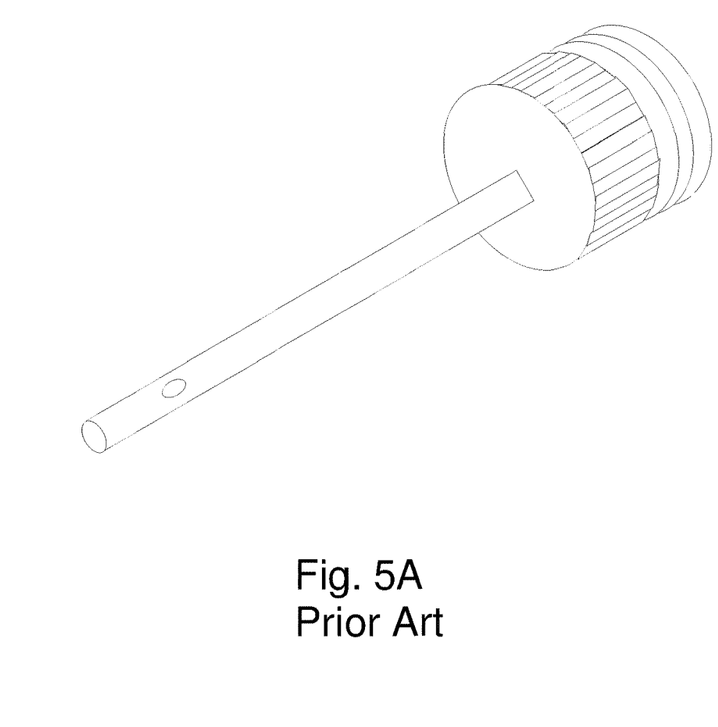
FIG. 5A shows a prior art needle inflation valve for a sports ball.
Figure 5B:
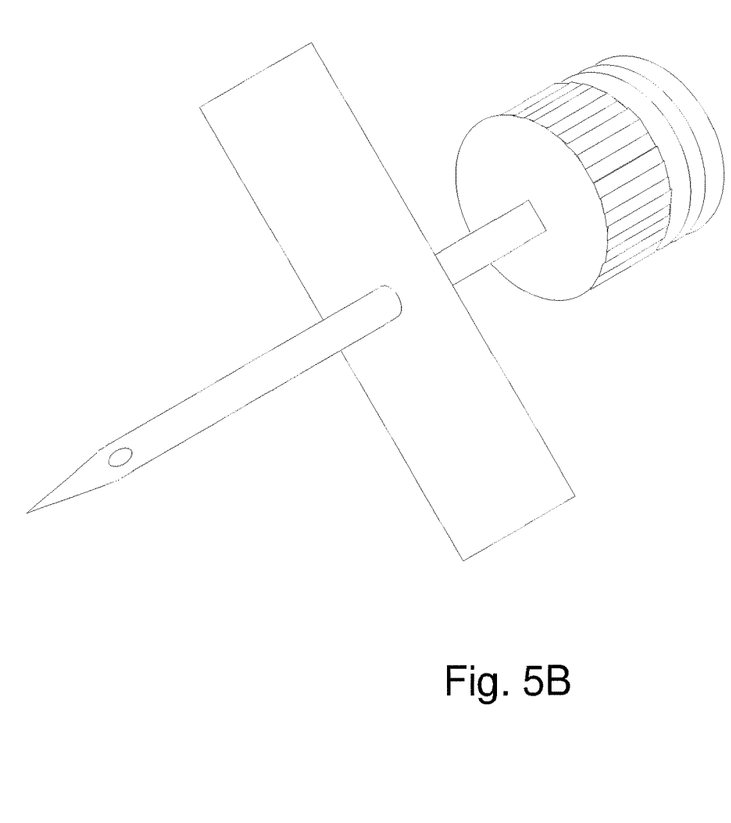
FIG. 5B shows a needle for chest inflation according to the present invention.

Most needles used to fill inflatable balls are just over 1 mm in outside diameter with outlets on the side of the tip and at the end of a blunt tip. See FIG. 5A. The needle design according to the present technology is similar in that it can be clamped or screwed into the regulator cap similar to the inflation needle for a ball, but the tip opening is closed and pointed with a conical tip (not the cutting tips of conventional hypodermic needles), as shown in FIG. 5B. This allows entry with a minimum of tissue damage. The opening is on the side, occupying about 90 degrees of arc so that the airflow can be directed down the trachea toward the lungs.

An inflation needle may thus be inserted into the cap, which provides about a 1 mm diameter cannula, with a side port and a sharpened tip for insertion through the skin, connective tissue and cartilage into the lumen of the trachea, below the vocal chords. The inflation needle may have a stop formed about one half inch from the tip, to prevent overinsertion of the needle into the trachea and into the dorsal wall of the trachea, (The internal diameter of the adult human trachea is about 1 inch.) The stop may be a plate or disk, and may be adjustable along the shaft of the needle, to accommodate different size patients. For example, the stop may be a transparent silicone rubber disk that press fits around the needle, which provides visibility for the caregiver during the procedure, while also preventing backsplash of body fluids.

A medical version of this system requires minimal modifications. Of course, the canister and valve cap should be clean and sterile, and avoid any liquid or powder lubricants. A medical valve cap would typically provide a Luer lock connector, though it is not required, and indeed incompatibility with intravenous tube sets may be an advantage.

The valve cap preferably has a trigger for activation, and may be limited to provide 0.5-1.5 liters per activation, and requiring a reset and second activation for more gas. A dual lumen cannula may be provided to permit feedback sensing of the gas pressure within the chest. In some cases, a single lumen may be used for both inflation and sensing. In this case, the regulator may automatically inflate the chest when the pressure is subatmospheric. In order to ensure that the gas is not injected accidentally, the initial blast of air may exhaust through the sensing port, ensuring that it is clear.

The needle preferably has a sharpened tip, e.g., having a conical or triangular profile (similar to the profile used in trochars), with an exhaust port facing downward. The stop/shield may have markings to show alignment, to ensure that the caregiver knows which way the port is facing.

The keys for inflation are a needle that can be safely inserted into the trachea between the cricoid and thyroid cartilages with a minimal chance of erroneous placement (too deep, not deep enough) and an opening that allows rapid filling at relatively low pressures without a sharply focused stream, to minimize the chance of tissue damage or penetration of the airway by an air jet. The space between the cricoid and thyroid cartilages is readily identifiable even in individuals with short necks, the space is relatively avascular to minimize complications, and it is the point at which the distance from skin surface to the interior of the airway is minimal. This insertion is technically into the larynx since it is between the thyroid and cricoid cartilages, not the trachea, but it will be below the point of obstruction due to laryngospasm or similar upper airway obstruction. Penetration through the rings of the trachea is variable and could lead to complications.

The goal is to deliver the full volume of gas quickly and allow it to pressurize the airway. When the obstruction is cleared, by whatever mechanism, the gas will be cleared by normal respiratory activity.

The acute intervention pulmonary inflation device is used as follows:

The device works to prevent pulmonary edema and, when using oxygen for inflation, to protect against hypoxemia during acute upper airway obstruction that can be life threatening within tens of seconds.

Because of the simplicity of design and use, it can be deployed by users of comparatively average skill, especially with some simple instructions. This is in contrast to the sophisticated intubation efforts performed in an emergency setting by highly trained physicians or technicians.

The device may have a system which presents prerecorded audio instructions, with a self-contained battery, activation button or sensor, speaker, and electronic integrated semiconductor "chip" device to produce the audible instructions.

Alternately, the device may be packaged with printed instructions in a kit, which also includes the gas cartridge, inflation valve, and needle. Because of the time criticality of the procedure, preferably, the device is preassembled, in a tray with a sealed membrane cover. The tray is preferred because the sharp needle requires protection, though a syringe-type cover may be used to protect the needle and the caregiver during preparation.

In some cases, the inflation device is reusable, though the needle is disposable. A reusable inflation device may have a disposable clear plastic sheet cover, like a bag, to ensure that it does not become soiled during use. When reusable, a canister or cartridge larger than 12-16 grams may be provided.

The device supports the individual for minutes, which means that a canister of gas plus the injection port can be small enough for high portability. In some cases, the device may be self-administered, though when the cause of the laryngospasm is a seizure, this may not be possible. The device is in any case meant for use "in the field" so that it can be deployed within the incredibly short time window before respiratory and/or cardiac arrest. Availability within medical facilities may of course be provided. The device may be provided along with automatic electronic defibrillator kits, or as part of a more generalized emergency kit.

Further, the intervention can be deployed in the field within the time that is likely to save a life. Cardiac rhythm changes occur within tens of seconds and respiratory and/or cardiac arrest in about 1 minute. Only a simple, portable intervention can be practical in this time frame.

In the case of seizure-induced laryngospasm that can be fatal, support needs to last several minutes before the obstruction spontaneously resolves. In the case of a choking incident, the intervention provides minutes for the work to remove the obstruction. In the case of acute airway obstruction in response to an allergic reaction, the device can be repeatedly used to support the individual for a longer period until a more stable solution can be established by trained emergency professionals.

Procedurally, the lung inflation device is used as follows:

1. As quickly as possible after recognizing that an upper airway obstruction exists, enable the gas canister/inflation needle.

2. Apply topical anesthetic around the point of entry (this is unnecessary if the individual has already lost consciousness, but useful in conscious individuals to minimize movements that may result in unnecessary trauma during insertion).

3. Insert the needle between the thyroid and cricoid cartilages, i.e. just below the lower border of the cartilage that forms the Adam's apple in the midline, to its built-in stop, ensuring that the needle tip is safely in the trachea.

4. Release the gas and hold the unit in place.

5. Release a second burst of gas after 2 minutes if obstruction is not cleared.

6. Release additional bursts of gas only if there seems to be leakage of gas as evidenced by actual gas leakage from the mouth or clear evidence of the chest returning to an uninflated size.

Example 2

An advanced version of the device permits the passage of a guide wire from the trachea up into the pharynx to facilitate rapid intubation of an individual with laryngospasm.

A guidewire with a loop (or blunt tip) may be extended from the needle upward, toward the larynx, past the vocal cords, which are constricted due to laryngospasm. As the guidewire emerges through the larynx, a caregiver may grasp and extend it, and then use the guidewire to properly place an endotracheal tube.

The portability of the device and intent for its use "in the field" by users of comparatively average skill rather than an emergency setting by highly trained physicians or technicians. This means that the risk of error is likely to be higher, and the end user will not be as equipped to deal with complications as emergency professionals.

The advanced version will therefore be typically used by medical professionals (EMT, emergency physicians, etc.) and requires training.

This more advanced version of the device performs the same function of penetrating the larynx and inflating the lungs, but also adds a feature that would facilitate the "reverse intubation" of a patient whose airway was closed by laryngospasm. In this version of the device, the kit contains a guide wire with a loop at the end, and a number 5 or 6 anode/corrugated endotracheal tube, and a 10 ml syringe.

After the initial burst of oxygen and hyperinflation, while chest compressions are done, the device is rotated 180 degrees so the opening points upward to the larynx and upper airway. The guide wire is passed through the opening until it reaches the pharynx. The EMT/operator bagging the patient can perform a finger sweep and retrieve the guide wire.

The eye of the flexible endotracheal tube is hooked to the loop of the guide wire, and the endotracheal tube pulled into the trachea and the lung inflation needle removed. The cuff of the ET tube is then inflated and the patient ventilated through it. The whole process should take less than 4 minutes afforded by the initial oxygen burst of the lung inflation device.

The guidewire/endotracheal tube option may be provided as part of an "Airway Kit" that could be kept at all places where AEDs are available. All hospital and health care personnel would be trained during CPR training in the use of this kit.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto. All references discussed herein are expressly incorporated herein by reference in their entirety.

REFERENCES

1. Amir, 1., S. Ashkenazi, T. Schonfeld, R. Weitz, and M. Nitzan, *Laryngospasm as a single manifestation of epilepsy*. Arch Dis Child, 1983. 58(2): p. 151-3.
2. Antoniuk, S. A., L. V. Oliva, I. Bruck, M. Malucelli, S. Yabumoto, and 1. L. Castellano, *Sudden unexpected, unexplained death in epilepsy autopsied patients*. Arq Neuropsiquiatr, 2001.59(1): p. 40-5.
3. Ead, H., *Review of laryngospasm and noncardiogenic pulmonary edema*. Dynamics, 2003. 14(3): p. 9-12.
4. Hotta, H., K. Koizumi, and M. Stewart, *Cardiac sympathetic nerve activity during kainic acid-induced limbic cortical seizures in rats*. Epilepsia, 2009. 50(4): p. 923-927.
5. Hotta, H., N. Watanabe, R. Orman, and M. Stewart, *Efferent and afferent vagal actions on conical blood flow and kainic acid-induced seizure activity in urethane anesthetized rats*. Auton Neurosci, 2010.156(1-2): p. 144-8.
6. Learning, J. M., T. E. Terndrup, and S. Ognibene, *Glottal patency during experimental cortical seizures in piglets*. Acad Emerg Med, 1999.6(7): p. 6827.
7. Mor, N., I. Naggar, O. Das, K. Nakase, 1. B. Silverman, K. Sundaram, M. Stewart, and R. Kollmar, *Quantitative video laryngoscopy to monitor recovery from recurrent laryngeal nerve injury in the rat*. Otolaryngol Head Neck Surg, 2014. 150(5): p. 824-6.
8. Morentin, B. and R. Alcaraz, [*Sudden unexpected death in epilepsy in children and adolescents*]. Rev Neurol, 2002. 34(5): p. 462-5.
9. Murray-Calderon, P. and M. A. Connolly, *Laryngospasm and noncardiogenic pulmonary edema*. J. Perianesth Nurs, 1997.12(2): p. 89-94.
10. Naggar, I., S. Uchida, H. Kamran, 1. Lazar, and M. Stewart, *Autonomic boundary conditions for ventricular fibrillation and their implications for a novel defibrillation technique*. J. Physiol Sci, 2012. 62(6): p. 479-92.
11. Naggar, I., J. Lazar, H. Kamran, R. Orman, and M. Stewart, *Relation of autonomic and cardiac abnormalities to ventricular fibrillation in a rat model of epilepsy*. Epilepsy Res, 2014.108(1): p. 44-56.
12. Saito, T., K Sakamoto, K Koizumi, and M. Stewart, *Repeatable focal seizure suppression: a rat preparation to study consequences of seizure activity based on urethane anesthesia and reversible carotid artery occlusion*. J Neurosci Methods, 2006.155(2): p. 241-50.
13. Sakamoto, K, T. Saito, R. Orman, K Koizumi, J. Lazar, L. Salciccioli, and M. Stewart, *Autonomic consequences of kainic acid-induced limbic cortical seizures in rats: peripheral autonomic nerve activity, acute cardiovascular changes, and death*. Epilepsia, 2008. 49(6): p. 982-96.
14. Salmo, E. N. and C. E. Connolly, *Mortality in epilepsy in the west of Ireland: a 10-year review*. Ir J Med Sci, 2002. 171(4): p. 199-201.
15. Stewart, *M.Is an abrupt "cerebral electrical shutdown II during a seizure the mechanism of SUDEP*? J. Neurol Neurosurg Psychiatry, 2008. jnnp.bmj.com/cgi/eletters/78/12/1395#3299, 12 Feb. 2008,
16. Stewart, M., *The urethane/kainate seizure model as a tool to explore physiology and death associated with seizures*, in Sudden Death in Epilepsy: Forensic and Clinical Issues, C. M. Lathers, et al., Editors. 2011, Taylor & Francis Group: Boca Raton, Fla. p. 627-644.
17. Tavee, J. and H. Morris, 3rd, *Severe postictal laryngospasm as a potential mechanism for sudden unexpected death in epilepsy: a near-miss in an EMU*. Epilepsia, 2008. 49(12): p. 2113-7.
18. Temdrup, T. E., M. E. Gregory, and W. E. Fordyce, *The role of the upper airway in contributing to respiratory responses during experimental seizures in piglets*. Pediatr Res, 1995. 38(1): p. 61-6.
19. Temdrup, T. E., A. Kadison, and P. Woo, *Glottal patency during experimental seizures in piglets*. Pediatr Res, 1995. 38(6): p. 932-7.
20. Udeshi, A., S. M. Cantie, and E. Pierre, *Postobstructive pulmonary edema*. J. Crit Care, 2010. 25(3): p. 508 e1-5.
21. Umbrain, V. and F. Cantu, *Acute pulmonary edema after laryngospasm*. Acta Anaesthesiol Belg, 1993. 44(4): p. 149-53.
22. Jackson, F. N., V. Rowland, and G. Corssen. "Laryngospasm-induced pulmonary edema." CHEST Journal 78.6 (1980): 819-821.
23. Deepika, Krishnaprasad, et al. "Negative pressure pulmonary edema after acute upper airway obstruction." Journal of clinical anesthesia 9.5 (1997): 403-408.
24. Lorch, D. G., and S. A. Satin. "Post-extubation pulmonary edema following anesthesia induced by upper airway obstruction. Are certain patients at increased risk?." CHEST Journal 90.6 (1986): 802-805.
25. Willms, D., and D. Shure. "Pulmonary edema due to upper airway obstruction in adults." CHEST Journal 94.5 (1.988): 1090-1092.

26. Herrick, Ian A., Bahnu Mahendran, and Foster J. Penny. "Postobstructive pulmonary edema following anesthesia." *Journal of clinical anesthesia* 2.2 (1990): 116-120.
27. Halow, K. D., and E. G. Ford. "Pulmonary edema following post-operative laryngospasm: a case report and review of the literature." *The American surgeon* 59.7 (1993): 443-447.
28. Glasser, S. A., and J. N. Siler. "Delayed onset of laryngospasm-induced pulmonary edema in an adult outpatient." *Anesthesiology* 62.3 (1985): 370.
29. Mehta, Vishvesh M., Gady Har-El, and Nira A. Goldstein. "Postobstructive pulmonary edema after laryngospasm in the otolaryngology patient." *The Laryngoscope* 116.9 (2006): 1693-1696.
30. Guffin, Thomas N., et al. "Acute postobstructive pulmonary edema." *Otolaryngology-Head and Neck Surgery* 112.2 (1995): 235-237.
31. Cascade, Philip N., Gaylord D. Alexander, and Donald S. Mackie. "Negative-pressure pulmonary edema after endotracheal intubation." *Radiology* 186.3 (1993): 671-675.
32. Timby, Jeffery, et al. "Mechanical causes of pulmonary edema," *Chest Journal* 98.4 (1990): 973-979.
33. Murray-Calderon, Patrice, and Maria A. Connolly. "Laryngospasm and noncardiogenic pulmonary edema." *Journal of PeriAnesthesia Nursing* 12.2 (1997): 89-94.
34. Mcgonagle, Martin, and Thomas L. Kennedy. "Laryngospasm induced pulmonary edema." *The Laryngoscope* 94.12 (1984): 1583-1585.
35. Anderson, Allen F., David Alfrey, and A. Brant. Lipscomb. "Acute pulmonary edema, an unusual complication following arthroscopy: a report of three cases." *Arthroscopy: The Journal of Arthroscopic & Related Surgery* 6.3 (1990): 235-237.
36. Kollef, Marin H., and Jerry Pluss. "Noncardiogenic Pulmonary Edema following Upper Airway Obstruction 7 Cases and a Review of the Literature." *Medicine* 70.2 (1991): 91-98.
37. Holmes, James R., Robert N. Hensinger, and Edward W. Wojtys. "Postoperative pulmonary edema in young, athletic adults." *The American journal of sports medicine* 19.4 (1991): 365-371.
38. Goldenberg, John D., et al. "Negative-pressure pulmonary edema in the otolaryngology patient." *Otolaryngology—Head and Neck Surgery* 117.1 (1997): 62-66.
39. Olsen, K. S. "Naloxone administration and laryngospasm followed by pulmonary edema." *Intensive care medicine* 16.5 (1990): 340-341.
40. Devys, Jean-Michel, et al. "Biting the laryngeal mask: an unusual cause of negative pressure pulmonary edema." *Canadian journal of anaesthesia* 47.2 (2000): 176-1.78.
41. Gluecker, Thomas, et al. "Clinical and radiologic features of pulmonary edema." *Radiographics* 19.6 (1999): 1507-1531.
42. Guinard, Jean-Philippe. "Laryngospasm-induced pulmonary edema." *International journal of pediatric otorhinolaryngology* 20.2 (1990): 163-168.
43. Westreich, Richard, et al. "Negative-pressure pulmonary edema after routine septorhinoplasty: discussion of pathophysiology, treatment, and prevention." *Archives of facial plastic surgery* 8.1 (2006): 8-15.
44. Fremont, Richard D., et al. "Postobstructive pulmonary edema: a case for hydrostatic mechanisms." *CHEST Journal* 131.6 (2007): 1742-1746.
45. Scarbrough, Frank E., et al. "Pulmonary edema following postoperative laryngospasm: case reports and review of the literature." *Anesthesia progress* 44.3 (1997): 110.
46. Wilson, Gregg W., and Nicholas G. Bircher. "Acute pulmonary edema developing after laryngospasm: report of a case." *Journal of oral and maxillofacial surgery* 53.2 (1995): 211-214.
47. Udeshi, Ashish, Shawn Michael Cantie, and Edgar Pierre. "Postobstructive pulmonary edema." *Journal of critical care* 25.3 (2010): 538-e1.
48. Lang, Scott A., et al. "Pulmonary oedema associated with airway obstruction." *Canadian journal of anaesthesia* 37.2 (1990): 210-218.
49. Mulroy, John J., et al. "Postictal pulmonary edema in children." *Neurology* 35.3 (1985): 403-403.
50. da Silva, Paulo Sergio Lucas, et al. "Negative-pressure pulmonary edema: a rare complication of upper airway obstruction in children." *Pediatric emergency care* 21.11 (2005): 751-754.
51. Galvis, Antonio G. "Pulmonary edema complicating relief of upper airway obstruction." *The American journal of emergency medicine* 5.4 (1987): 294-297.
52. BVSC, A S TUTE, et al. "Negative Pressure Pulmonary Edema as a Post-Anesthetic Complication Associated With Upper Airway Obstruction in a Horse." *Veterinary Surgery* 25.6 (1996): 519-523.
53. Bhavani-Shankar, K., Nada Saliba Hart, and Phillip S. Mushlin. "Negative pressure induced airway and pulmonary injury." *Canadian journal of anaesthesia* 44.1 (1997): 78-81.
54. Tarrac, Shauna Ely. "Negative pressure pulmonary edema—a postanesthesia emergency." *Journal of PeriAnesthesia Nursing* 18.5 (2003): 317-323.
55. Daniel Friedman, Lawrence J Hirschm "Sudden Unexpected Death in Epilepsy—An Overview of Current Understanding and Future Perspectives", European Neurological Review, 2012; 7(1):67-71 DOI:10.17925/ENR.2012.07.01.67 (2012).
56. Tavee J, Morris H 3rd, Epilepsia, 2008; 49(12):2113-7. (2008).

The invention claimed is:

1. A device for relief of negative lung pressure after acute upper airway obstruction, comprising:
   a canister which serves as a source of compressed gas suitable for inflation of n lungs;
   a valve, configured to control a release of the compressed gas from the canister;
   a hollow inflation needle having a diameter of about 1 mm and having a sharpened, closed tip configured to pierce through the skin and cricothyroid cartilage into the larynx or the through the skin and tracheal cartilage into the trachea, and a valve interface configured to receive compressed gas from the valve of between about 1-60 liters per minute; and
   a stop configured to establish an insertion limit for the inflation needle into a human larynx or trachea,
   wherein the valve is configured to supply a sufficient amount of compressed gas to alleviate a negative pressure condition in the larynx without causing pneumothorax.

2. The device according to claim 1, wherein the hollow inflation needle has a closed tip and a side exhaust port for the compressed gas.

3. The device according to claim 1, further comprising a guidewire configured to pass through the inflation needle.

4. The device according to claim 3, wherein the guidewire has a looped end.

5. The device according to claim 4, further comprising an endotracheal tube, having a hook adapted for connection to the looped end.

6. The device according to claim 1, wherein valve interface is configured to permit a flow of compressed gas of at least 3 liters per minute from the valve to the hollow inflation needle, the valve being manually controlled to initiate and cease the flow.

7. The device according to claim 1, wherein the compressed gas is compressed air.

8. The device according to claim 1, wherein the compressed gas consists essentially of anoxic gas.

9. The device according to claim 1, wherein the valve comprises a finger trigger.

10. The device according to claim 9, wherein the source of compressed gas comprises a cartridge having a threaded neck for attachment to the valve.

11. The device according to claim 1, wherein the source of compressed gas comprises between about 4-30 grams of gas.

12. The device according to claim 1, wherein the valve comprises a pressure regulator.

13. The device according to claim 1, wherein the valve comprises a timer configured to limit a time of flow of the compressed gas through the hollow inflation needle.

14. The device according to claim 1, wherein the inflation needle has an internal surface inclined with respect to an axis of the needle to deflect an inserted guidewire out through a sidewall aperture.

15. A method for relieving negative lung pressure after acute upper airway obstruction of a human, comprising:
   providing a device comprising a source of compressed gas suitable for inflation of human lungs; a control, configured to selectively control a flow of the compressed gas sufficient to alleviate a negative pressure condition in a larynx of the human, without causing pneumothorax;
   a hollow inflation needle having a diameter of about 1 mm and having a sharpened, closed tip configured to pierce through the skin and cricothyroid cartilage into the larynx or through the tracheal cartilage into the trachea, an interface configured to receive a controlled flow of compressed gas from the control of between about 1-60 liters per minute; and a stop configured to establish an insertion limit for the inflation needle into a human trachea;
   assessing an upper airway status of the human;
   inserting the inflation needle through the skin and cricothyroid cartilage into the larynx or tracheal cartilage into the trachea; and
   controlling inflation from the source of compressed gas, through the inflation needle, into the larynx or trachea, to alleviate the negative lung pressure.

16. The method according to claim 15, further comprising inserting a guidewire having a looped end through the inflation needle into the larynx or trachea; and extending the guidewire upward through the larynx, past the upper airway obstruction.

17. The method according to claim 16, further comprising:
   providing a tube, having a hook adapted for connection to the looped end;
   connecting the looped end to the tube; and
   guiding the tube through the upper airway obstruction by retracting the guidewire.

18. The method according to claim 15, wherein the control comprises a valve activated with a finger trigger, further comprising depressing the finger trigger to initiate a flow of gas into the larynx or trachea.

19. The method according to claim 15, wherein the control comprises a valve having a pressure regulator, further comprising sensing a pressure within the larynx below the upper airway obstruction, and controlling a flow of gas dependent on the sensed pressure.

20. A method of preventing pulmonary edema from acute upper airway obstruction, comprising:
   providing a source of compressed gas suitable for relief of negative pressure in a larynx after the upper airway obstruction, and inflation of lungs without substantial acute toxicity or causing pneumothorax;
   assessing a respiratory status;
   inserting a hollow inflation needle having a diameter of about 1 mm and having a sharpened, closed tip, through the skin into the larynx or trachea; and
   controlling a release of the compressed gas with a valve, at a rate of between about 1-60 liters per minute, to relieve the negative pressure.

* * * * *